(12) United States Patent
Husemann et al.

(10) Patent No.: US 11,124,753 B2
(45) Date of Patent: Sep. 21, 2021

(54) SYSTEM, DEVICE AND METHOD FOR RECEIVING A DISPOSABLE BAG

(71) Applicant: Sartorius Stedim Biotech GmbH, Goettingen (DE)

(72) Inventors: Bernward Husemann, Goettingen (DE); Simon Topp-Manske, Lohfelden (DE); Bjorn Nickel, Hessisch Lichtenau (DE); Marco Leupold, Kassel (DE)

(73) Assignee: Sartorius Stedim Biotech GmbH

( * ) Notice: Subject to any disclaimer, the term of this patent is extended or adjusted under 35 U.S.C. 154(b) by 106 days.

(21) Appl. No.: 15/577,822

(22) PCT Filed: Mar. 8, 2016

(86) PCT No.: PCT/EP2016/000407
§ 371 (c)(1),
(2) Date: Nov. 29, 2017

(87) PCT Pub. No.: WO2016/192824
PCT Pub. Date: Dec. 8, 2016

(65) Prior Publication Data
US 2018/0163164 A1      Jun. 14, 2018

(30) Foreign Application Priority Data

Jun. 2, 2015  (DE) .......................... 102015007061.4

(51) Int. Cl.
*C12M 1/00*        (2006.01)
*C12M 3/00*        (2006.01)
(Continued)

(52) U.S. Cl.
CPC ............ *C12M 23/14* (2013.01); *C12M 23/34* (2013.01); *C12M 23/48* (2013.01); *C12M 41/12* (2013.01);
(Continued)

(58) Field of Classification Search
CPC ....................................................... C12M 23/14
(Continued)

(56) References Cited

U.S. PATENT DOCUMENTS 1,950,360 A * 3/1934 Laabs ..................... C11B 13/00
                                                        554/22
3,980,131 A * 9/1976 Perle ......................... A61L 2/24
                                                        165/61
(Continued)

FOREIGN PATENT DOCUMENTS

DE      7613603      8/1976
DE      4028871      3/1992
(Continued)

OTHER PUBLICATIONS

Lide, ed., CRC Handbook of Chemistry and Physics, Internet Version, 2005, <http://www.hbcpnetbase.com>, CRC Press (Year: 2005).*

(Continued)

*Primary Examiner* — Holly Kipouros
(74) *Attorney, Agent, or Firm* — Gerald E. Hespos; Michael J. Porco; Matthew T. Hespos

(57) ABSTRACT

A system for receiving a disposable bag (44) has a receiving container (10) with a container interior for receiving the disposable bag (44) and a temperature-control hollow wall (20) that at least partially surrounds the container interior of the receiving container (10). A temperature-control unit controls the temperature of the container interior by will a temperature-control medium arranged in the temperature-control hollow wall (20) at a maximum pressure of about 1 bar.

14 Claims, 6 Drawing Sheets

(51) Int. Cl.
*C12M 1/02* (2006.01)
*C12M 1/36* (2006.01)
*C12M 1/34* (2006.01)
*F28D 1/06* (2006.01)
*B01F 15/00* (2006.01)
*C12M 1/06* (2006.01)
*F28D 21/00* (2006.01)

(52) U.S. Cl.
CPC ............ *C12M 41/18* (2013.01); *C12M 41/22* (2013.01); *F28D 1/06* (2013.01); *B01F 15/0085* (2013.01); *B01F 2215/0073* (2013.01); *C12M 27/02* (2013.01); *F28D 2021/0078* (2013.01)

(58) Field of Classification Search
USPC ....................................................... 435/289.1
See application file for complete search history.

(56) References Cited

U.S. PATENT DOCUMENTS

| | | | | |
|---|---|---|---|---|
| 4,746,615 A * | 5/1988 | Buchholz | ............... | C12M 25/20 435/296.1 |
| 2004/0062140 A1 * | 4/2004 | Cadogan | ................... | B01F 7/18 366/144 |
| 2005/0272146 A1 | 12/2005 | Hodge et al. | | |
| 2006/0196501 A1 * | 9/2006 | Bibbo | ................... | C12M 23/14 128/200.23 |
| 2009/0151240 A1 * | 6/2009 | Kayama | ................ | A01G 33/00 47/1.4 |
| 2010/0075405 A1 * | 3/2010 | Broadley | ............... | C12M 41/22 435/286.1 |
| 2011/0210696 A1 | 9/2011 | Inoue | | |
| 2013/0089925 A1 * | 4/2013 | Damren | ................ | C12M 41/24 435/303.3 |
| 2015/0029815 A1 * | 1/2015 | Gebauer | ................ | C12M 23/14 366/144 |
| 2015/0299641 A1 * | 10/2015 | Galliher | ............... | F28F 9/0131 435/298.1 |

FOREIGN PATENT DOCUMENTS

| | | |
|---|---|---|
| DE | 102005006055 | 8/2006 |
| GB | 190321371 | 10/1904 |
| WO | 2006032084 | 3/2006 |
| WO | 2015039034 | 3/2015 |

OTHER PUBLICATIONS

Mohrig et al., Techniques in organic chemistry, 2006, W.H. Freeman and Company (Year: 2006).*
International Preliminary Report on Patentability for Application No. PCT/EP2016/000407 dated Dec. 5, 2017.
International Search Report dated Jul. 5, 2016.
European Examination Report dated Aug. 16, 2019.

* cited by examiner

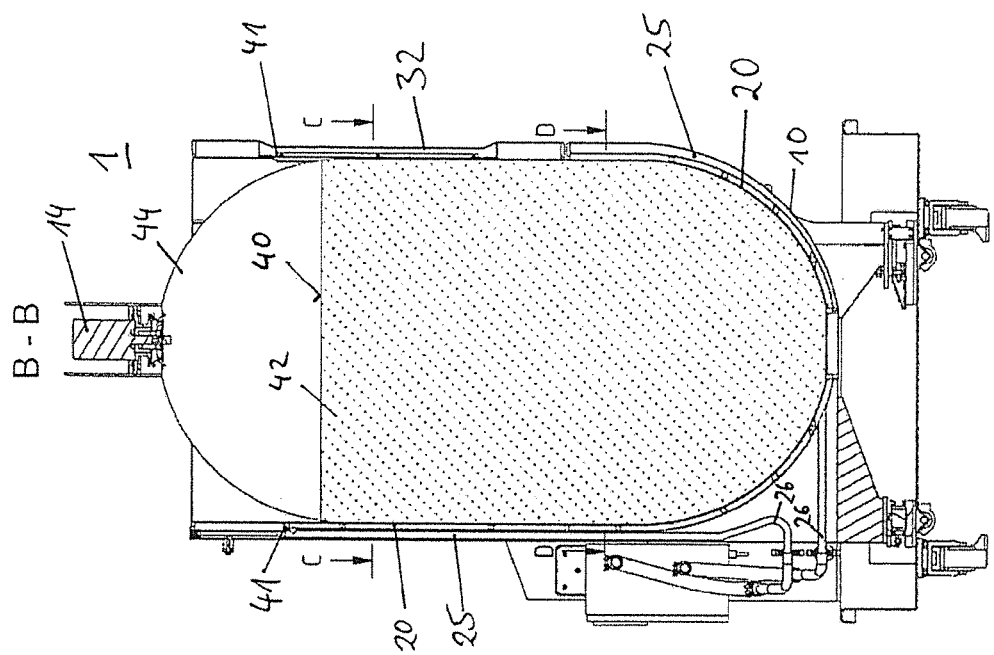
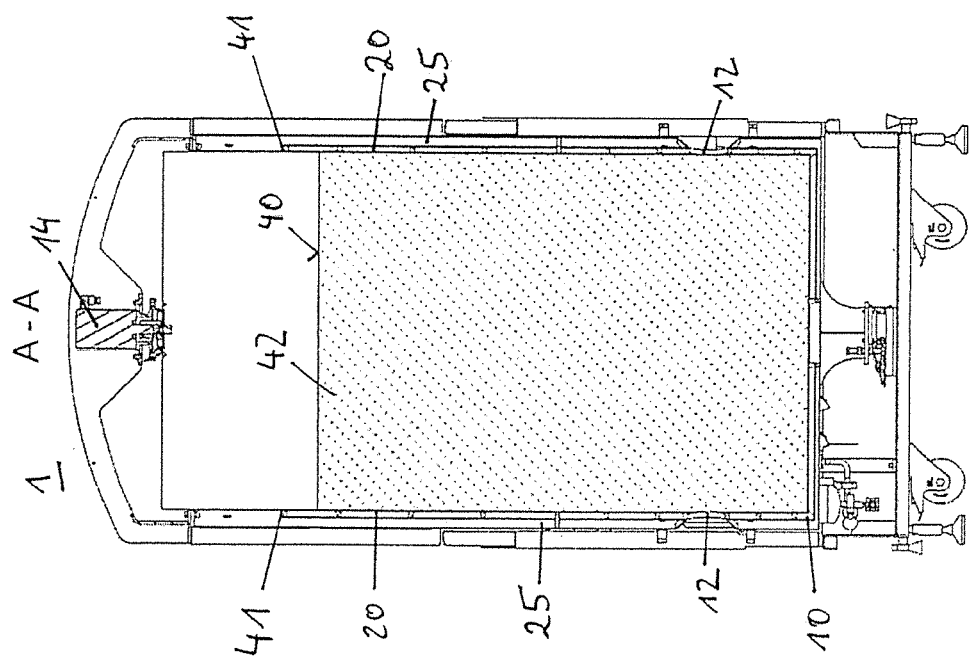
Fig. 4B
Fig. 4A

D - D

C - C

SYSTEM, DEVICE AND METHOD FOR RECEIVING A DISPOSABLE BAG

BACKGROUND

Field of the Invention

The invention relates to a system, an apparatus, and a method for receiving a disposable bag.

Related Art

Bioreactors and pallet tanks are used as apparatuses for receiving and storing biological media, such as fluids. Biological media can be furnished in disposable bags which can hold a volume of a few liters to several hundred liters. The biological media are placed in a bioreactor inside a disposable bag, and heated to a predetermined temperature over a predetermined period of typically several hours. Furthermore, different examinations of the biological medium can be performed in such a bioreactor.

A bioreactor may be manipulated under clean room conditions. As a result, particularly high demands are placed on quality assurance for the use of the bioreactor. In particular, the temperature control of the biological medium is subjected to stringent quality requirements, since—for example when temperature control fluids are used at high pressure—specific dangerous conditions may arise during the manipulation of the bioreactor. When temperature control fluids are handled under high pressure, well-defined safety precautions must be taken.

The problem addressed by the invention is that of providing a possibility of the aforementioned type for receiving a disposable bag, with improved and/or simplified temperature control.

SUMMARY OF THE INVENTION

A first aspect relates to a system for receiving a disposable bag, having a receptacle with a receptacle interior for receiving the disposable bag, and having a hollow temperature control wall which at least partially surrounds the receptacle interior. A temperature control unit controls the temperature of the receptacle interior by means of a temperature control medium disposed in the hollow temperature control wall, at a maximum pressure of about 1 bar, preferably a maximum of about 0.5 bar.

The system can be designed as a bioreactor and/or pallet tank, and can be designed to receive disposable bags with a volume of about 1 liter to about 2000 liters—preferably with a volume of about 200 liters to about 1000 liters. The system can particularly be adapted to receive disposable bags in which a biological medium such as a fluid is held, said fluid being stored, temperature controlled, and/or otherwise analyzed in the system for a predetermined period of time. The system according to the first aspect can, in particular, comprise an apparatus according to the second aspect.

The receptacle of the system furnishes the receptacle interior, which is designed to receive the disposable bag. The receptacle interior can be designed to receive a predetermined type of disposable bag—for example, a disposable bag of a predetermined manufacturer and/or with a predetermined fill volume. In this case, the container walls of the receptacle define the receptacle interior. The container walls of the receptacle need not necessarily entirely surround and/or bound the receptacle interior. For instance, the receptacle can comprise a stirring opening through which a stirring device can be connected to the disposable bag in the receptacle interior. Such a stirring device is preferably constructed on the upper end of the receptacle. The receptacle can therefore be constructed particularly without a lid, and/or open at the top.

The terms "top," "bottom," "lateral," "vertical," "horizontal," "height," etc. used in the context of this invention take the earth as the frame of reference on which the system or the apparatus is arranged in an operating position.

The disposable bag is preferably inserted into the receptacle in such a manner that it rests on a floor of the receptacle and is in direct physical contact with the container walls of the receptacle—in particular in contact with the floor of the receptacle and/or the container walls adjacent to the floor.

The hollow temperature control wall is constructed in the container walls of the receptacle, in a closed temperature control loop. The hollow temperature control wall can be constructed as part of the receptacle walls. The hollow temperature control wall can be designed as a double wall with an inner and an outer temperature control wall. The inner temperature control wall can face the receptacle interior of the receptacle, and the outer temperature control wall can face away from the receptacle interior.

The temperature control medium is formed in a hollow space between the inner temperature control wall and the outer temperature control wall. The temperature control unit uses the temperature control medium to control the temperature of the receptacle interior, in particular the contents of the disposable bag—i.e., the biological medium. For this purpose, a controller may be provided, by means of which the temperature and/or pressure of the temperature control medium in the hollow temperature control wall can be controlled and/or adjusted. The controller can be designed as part of the temperature control unit. The temperature control unit can thus comprise the controller and/or the temperature control medium arranged in the hollow temperature control wall.

The interior of the hollow temperature control wall can be designed as an open cavity, or with at least one flow guide element for guiding the flow of the temperature control medium through the hollow temperature control wall.

The two walls of the hollow temperature control wall—that is, an inner temperature control wall and an outer temperature control wall—can be spaced apart from each other at a distance of a few millimeters—for example, between 5 mm and 20 mm.

The inner side of the hollow temperature control wall—that is, the inner temperature control wall facing the receptacle interior—can be constructed directly bounding the receptacle interior. In other words, no additional element of the system need be placed between the receptacle interior and the hollow temperature control wall. In other words, the hollow temperature control wall can (at least partially) directly surround and/or bound the receptacle interior.

In this case, "at least partially surround" means that the hollow temperature control wall surrounds at least 40% of the receptacle interior, forming its outer surface, and preferably at least 60%, particularly preferably at least 70%, and particularly preferably at least 80%. In particular, this can mean that the receptacle interior is completely surrounded and/or bounded and/or temperature-controlled, up to its upper lid region and optionally a view window and/or a door opening, by the hollow temperature control wall.

The temperature control medium in the hallow temperature control wall is brought to a pressure which is at most about 1 bar, preferably at most about 0.5 bar. With a maximum pressure of about 1 bar or 0.5 bar, or less, the temperature control medium is no longer considered a high-pressure medium, depending on the applicable pressure vessel guidelines being used. According to the ASME ("American Society of Mechanical Engineers" for the American economic area) guideline, the maximum pressure is 1 bar; according to the PED ("Pressure Equipment Directive" for the European Economic Area) guideline, the maximum pressure is 0.5 bar. The specifications for a high-pressure medium are particularly strict because there are special safety risks which arise in the handling and/or use of a high-pressure medium. Due to the use of a temperature control medium at such a low pressure, the safety risk of the temperature control process is significantly reduced. In particular, the temperature control medium can be at a pressure which is, at most, exactly 0.5 bar, or is always less than 0.5 bar.

In general, the temperature control medium can be designed as a fluid, such as a liquid or a gas, for example, which is kept in a closed temperature control loop. The hollow temperature control wall of the receptacle constitutes at least a portion of this temperature control loop.

According to one embodiment, the temperature control unit brings the temperature control medium in the hollow temperature control wall, in a closed temperature control loop, to a predetermined maximum pressure of about 1 bar, or about 0.5 bar. The temperature control unit therefore comprises adjusting means, such as a controller, to adjust the pressure of the temperature control medium. In particular, the temperature control unit is designed and included to set the pressure of the temperature control medium to a maximum of about 0.5 bar, thereby reducing the safety risk.

According to one embodiment, the temperature control unit uses the temperature control medium, which has a pressure of about 0.20 bar to about 0.45 bar, to control the temperature of the receptacle interior. In this pressure range, the temperature control medium is not a high-pressure medium with the associated safety risks. However, it still has a pressure which is sufficiently high to ensure adequate performance for the temperature control of the receptacle interior.

A second aspect relates to an apparatus for receiving a disposable bag, having a receptacle with a receptacle interior for receiving the disposable bag. A hollow temperature control wall at least partially surrounds the receptacle interior of the receptacle. The hollow temperature control wall is designed and included for the purpose of accommodating a temperature control medium, at a pressure of at most about 1 bar, preferably at most about 0.5 bar, used to control the temperature of the receptacle interior.

The apparatus can be designed as a bioreactor which can be designed to receive disposable bags having a volume of several hundred liters—by way of example, a volume of 1 liter up to 2000 liters.

The apparatus according to the second aspect may be constructed as part of a system according to the first aspect. Thus, all statements made here—and in particular, the embodiments discussed—in connection with the first aspect, also relate to the apparatus according to the second aspect. In addition, all embodiments described in connection with the apparatus according to the second aspect can also be implemented in the system according to the first aspect.

In the apparatus according to the second aspect, the temperature control medium can be disposed in the hollow temperature control wall. The hollow temperature control wall is specially designed and included to accommodate a temperature control medium at a maximum pressure of about 0.5 bar. For this purpose, a controller may be provided, by means of which the temperature and/or pressure of the temperature control medium in the hollow temperature control wall can be controlled and/or adjusted. The controller can be designed as part of the apparatus. The apparatus can thus comprise the controller and/or the temperature control medium disposed in the hollow temperature control wall.

Due to the use of a temperature control medium at such a low pressure, the safety risk of the temperature control process is significantly reduced.

According to one embodiment, the hollow temperature control wall is designed and included to accommodate the temperature control medium to control the temperature of the receptacle interior at a pressure of about 0.20 bar to about 0.45 bar. The temperature control medium in the hollow temperature control wall can be at a pressure of about 0.20 bar to about 0.45 bar when performing the temperature controlling function. In this pressure range, the temperature control medium is not a high-pressure medium with the associated safety risks. However, it still has a pressure which is sufficiently high to ensure adequate performance for the temperature control of the receptacle interior.

In one embodiment, at least one flow guide element, for guiding the flow of the temperature control medium through the hollow temperature control wall, is arranged in the hollow temperature control wall. In particular, a plurality of flow elements can be included for this purpose. The flow element can be designed as a partition wall which runs, at least in sections, substantially in a straight line, and which defines and/or determines at least sections of a flow path in the interior of the hollow temperature control wall. The flow element can be designed, by way of example, as a spiral conduit through the hollow temperature control wall. The flow element can prevent the formation of an unevenly distributed flow pattern in the hollow temperature control wall. Without the flow element, the temperature control medium could flow in the hollow temperature control wall substantially in a straight line from a temperature control medium inlet to a temperature control medium outlet. With the flow element, the flow can be diverted through the hollow temperature control wall. In particular, the temperature control performed by the temperature control medium can be improved by the flow element(s), due to the fact that the recently temperature-controlled temperature control medium substantially flows through the entire hollow temperature control wall in an even manner.

According to one embodiment, the at least one flow guide element is designed and/or arranged at an angle, in such a manner that the temperature control medium flows through the hollow temperature control wall with a continuous, vertical direction component. In this case, 'at an angle' means that the flow guide element is not exclusively horizontal, which would produce a substantially horizontal portion of the flow route. Rather, the flow guide element extends vertically—at least in addition to its remaining configuration. This produces a flow route through the hollow temperature control wall with at least a vertical component. The flow is preferably routed with both a vertical and a horizontal direction component, so as to guide the temperature control medium as uniformly and efficiently as possible through the hollow temperature control wall. In this case, the horizontal component of the flow route can be made greater than the vertical component, preferably even at least twice or at least three times as large. In particular, the flow can be routed from a temperature control medium inlet arranged on a lower end of the hollow temperature control wall to a temperature control medium outlet arranged on an upper end of the hollow temperature control wall, and/or vice versa. In order to prevent the formation of air bubbles in the flow route, the flow route has a substantially continuous vertical directional component. This can reduce disruption of the temperature control process due to air inclusions, in particular independently of a flow and/or a direction of flow of the temperature control medium. As a result, the temperature control effect can be improved.

According to one embodiment, a collecting chamber with a ventilation outlet and a temperature control medium outlet which is separate therefrom are arranged at an upper end of the hollow temperature control wall. The separate temperature control medium outlet can be designed, for example, as an overflow and/or return flow via which the temperature control medium is conveyed out of the hollow temperature control wall. The ventilation outlet can be arranged on an upper end of the collecting chamber, thereby connecting to a position where air gathers in the hollow temperature control wall. As a result, any air present in the loop is vented as easily as possible, rather than being routed back continuously through the entire cooling loop. The ventilation outlet can be adjusted to the pressure which is set in the hollow temperature control wall. In addition, a target pressure in the hollow temperature control wall can be controlled and/or regulated via the ventilation outlet.

According to one embodiment, the hollow temperature control wall is formed in such a manner that it substantially entirely surrounds and/or bounds at least a lower third of the receptacle interior. The floor of the receptacle and the container walls adjacent to the floor are located in the lower third of the receptacle interior. The hollow temperature control wall is constructed in the receptacle walls of the receptacle in at least this lower third. A stable receptacle trough can be constructed in the lower third. As such, the temperature is controlled by the temperature control medium at least entirely around the lower third of the receptacle interior—that is, along the entire lateral wall circumference of the receptacle—and substantially entirely up to, optionally, the floor view window arranged in the receptacle wall.

According to one embodiment, the hollow temperature control wall is designed in such a manner that it controls the temperature of, and/or surrounds and/or bounds, the receptacle interior to above a predetermined fill level in the receptacle. The apparatus and, in particular, the receptacle, are designed to receive a predetermined disposable bag. This disposable bag comprises a predetermined volume of a biological medium. As such, the predetermined fill level in the receptacle corresponds to the height of the fill level of the biological medium in the receptacle when one of the predetermined disposable bags with the biological medium is arranged in the receptacle interior.

As such, the hollow temperature control all surrounds and/or bounds the receptacle interior not only up to the predetermined fill level, but beyond and above this fill level. Typically, the temperature of an upper part, such as a lid of a bioreactor, is not controlled itself, since the biological medium is not filled up to the lid of the bioreactor and thus does not contact the lid. As such, controlling the temperature of the lid and/or the upper part of the bioreactor would not control the temperature of the biological medium—rather only the air present in the apparatus, which may potentially escape through an opening in the container. For this reason, temperature control of the air in the bioreactor is generally avoided, and only performed up to, at most, the fill level. However, more particularly, when the biological medium in the bioreactor is stirred, the biological medium can rise above the predetermined fill level in the receptacle. This particularly occurs when a stirring movement produces a funnel-shaped pattern due to centrifugal forces. The hollow temperature control wall is constructed, in this embodiment of the apparatus, significantly above the predetermined fill level, and is thus also able to control the temperature of the biological medium in the interior of the disposable bag to above the predetermined fill level, even during a stirring movement. This improves the temperature control.

In a further development of this embodiment, the hollow temperature control wall is designed in such a manner that it controls the temperature of the receptacle interior, and/or surrounds and/or bounds the same, at least to about 1 cm, and at most about 20 cm, preferably about 5 cm to about 12 cm, above the predetermined fill level in the receptacle. This level has been found to be a suitable average both in terms of maximum temperature control efficiency for the biological medium, and as regards minimizing temperature control performance losses due to the air in the upper region of the receptacle.

According to one embodiment, the apparatus comprises at least one relief valve for adjusting and/or limiting the pressure of the temperature control medium in the hollow temperature control wall. The relief valve can be constructed as a component of a controller and/or a temperature control unit. The at least one relief valve functions to ensure that the temperature control medium does not exceed a predetermined target pressure in the hollow temperature control wall—for example, a target pressure of approximately or exactly 0.5 bar.

According to one embodiment, the apparatus comprises an electric heater with a heat exchanging connection to the temperature control medium. The electric heater can be controlled and/or adjusted via a controller of the temperature control medium. The electric heater can be designed as an internal heater—constructed, by way of example, directly adjacent to the hollow temperature control wall, in the interior of the hollow temperature control wall, and/or in the temperature control loop of the temperature control medium. The electric heater can be designed, for example, as a heating cartridge. The electric heater functions to adjust the temperature of the temperature control medium, and therefore to set a target temperature for the receptacle interior.

According to one embodiment, the temperature control medium can be conveyed through an external heat exchanger. The heat exchanger can be designed as a separate component or as a component of the apparatus. The heat exchanger can be designed and included both to cool and to heat the temperature control medium. A heat exchange with an external temperature control medium can occur in the heat exchanger—for example, under high pressure. The heat exchanger enables the use of external heating media which would be too aggressive to be conveyed through the receptacle. Special security measures need to be observed in this case—merely for monitoring and/or controlling the external temperature control medium, not for monitoring the internal temperature control medium in the hollow temperature control wall. This simplifies the handling of the temperature control medium. The external temperature control medium can be present at high pressures up to 10 bar, so as to achieve high heat exchange efficiency. In this embodiment, one or more isolated temperature control lines can be included, with the internal temperature control medium conveyable through the same to the external heat exchanger and back to the hollow temperature control wall.

According to one embodiment, an insulation is at least partially formed on the side of the hollow temperature control wall facing away from the receptacle interior—for example, on the outer temperature control wall—insulating the hollow temperature control wall from the outside. Preferably, the insulation is designed in such a manner that it completely insulates the hollow temperature control wall from the outside. This reduces energy loss due to heat transfer of the temperature control medium to the outside air—that is, air outside the receptacle interior. This also simultaneously ensures that the temperature of the temperature control medium is thus delivered substantially exclusively inwards—that is, in the receptacle interior—and therefore to the biological medium found in the disposable bag. The insulation can be designed as an air layer, as a vacuum, or as an insulating material, such as insulating wool. The insulation can be designed in such a manner that at least the hollow temperature control wall is fully insulated from the outside.

In a further development of this embodiment, the insulation is at least partially disposed in a hollow insulation wall which is constructed on the side of the hollow temperature control wall which faces away from the receptacle interior. The receptacle wall of the receptacle therefore has, at least partially, a double cavity—in other words, three partition walls arranged successively from inside to outside. The temperature control medium is arranged in the first hollow space as viewed from the receptacle interior: the hollow temperature control wall. The insulation is arranged in the second hollow wall as viewed from the receptacle interior: the hollow insulation wall. As such, the arrangement from inside to outside can include:
1. an inner temperature control wall adjacent to the receptacle interior,
2. adjacent thereto, the temperature control medium in the hollow temperature control wall,
3. adjacent thereto, the outer temperature control wall, which can be designed as an inner insulation wall at the same time,
4. adjacent thereto, the insulation in the hollow insulation wall, and
5. adjacent there, an outer insulation wall.

This provides a particularly efficient temperature control and insulation of the receptacle interior.

According to one embodiment, the receptacle has an openable door through which the disposable bag can be inserted in a substantially horizontal direction into the receptacle interior. The door has at least one door hinge on which the door is mounted in a manner allowing rotation. The door can be opened, and grants access to the receptacle interior when open. The door is designed as a part of the receptacle wall of the receptacle. The door is constructed in a side wall of the receptacle, and therefore allows access into the receptacle interior in a substantially horizontal direction. This allows the disposable bag to be inserted into the receptacle interior, and/or taken out of the receptacle interior, in a substantially horizontal direction. The remainder of the receptacle can be solid. In particular, the remaining side walls of the receptacle can be designed to be dimensionally stable without further opening possibilities. This increases the overall stability of the receptacle compared to conventional bioreactors in the prior art, which are completely divided into two halves during insertion of the disposable bag. It has been found that even one door is sufficient to enable easy and reliable insertion of a disposable bag into the receptacle, Rather, the door actually simplifies the insertion of the disposable bag. The door can be designed as a single-panel door or as a double door.

In a further development of the embodiment, the receptacle is substantially designed in the form of a cylinder arranged vertically, wherein the door is constructed in the cylinder shell of the receptacle over a cylindrical sector of about 80° to about 150°. The axis of the cylinder of the receptacle is arranged substantially vertically in the reference frame of the earth. An embodiment of the door, and therefore of an equally large door opening, over the angular range of about 80° to about 150° is particularly advantageous in several respects. The door width extends over less than half of the cylinder circumference, and is thus smaller than a cylinder sector with 180°. On the one hand, this ensures high static stability of the receptacle. On the other hand, this dimensioning of the door enables a fixing of lines, etc. in a vertical orientation on opposing, stationary container walls—for example, for mounting, supplying and/or controlling a stirring device. On the other hand, the door with this dimensioning is large enough to ensure sufficiently simple access into the receptacle interior. Preferably, the door, and therefore an equally large door opening, extends over a cylinder sector of 90° to 120° in the receptacle wall of the receptacle.

In the embodiment with the door, the hollow temperature control wall and/or the insulation can also be formed in the door. By way of example, the hollow temperature control wall can be excluded from the space inside the door, while the insulation is present in the door. Alternatively, the hollow temperature control wall can be present in both the receptacle wall of the receptacle and in the door—specifically on the side of the door facing the receptacle interior. This enables controlling the temperature of the receptacle interior in the region of the door. The insulation can also be formed on the outside of the door—for example, inside a hollow insulation wall as described above. Alternatively, the door can have only insulation, but not a hollow temperature control wall. In this case, one or more temperature control lines can be included in or on the door hinge (or optionally, the door hinges) of the door, for example, to convey the temperature control medium into the hollow temperature control wall. This enables temperature control not only of the receptacle walls, but also of the door itself, which increases the overall temperature control effect and improves temperature control and/or insulation of the receptacle interior.

A third aspect relates to a method for receiving a disposable bag, having the steps:
receiving a disposable bag in a receptacle interior of a receptacle, and
controlling the temperature of the disposable container received in the receptacle interior, by means of a temperature control medium arranged in a hollow temperature control wall which at least partially surrounds the receptacle interior of the receptacle,
wherein the temperature control medium in the hollow temperature control wall s at a pressure of at most about 1 bar, and preferably about 0.5 bar.

The method can be carried out using an apparatus according to the second aspect and/or using a system according to the first aspect, by way of example. Accordingly, all statements made in connection with the first and second aspect, and particularly the embodiments discussed, also relate to the method according to the third aspect.

The invention is described below in greater detail with reference to embodiments shown in the figures. Individual features of the embodiments shown in the figures can be implemented in other embodiments. Like reference numerals designate like or similar features of the embodiments.

BRIEF DESCRIPTION OF THE DRAWINGS

FIG. 4A is a vertical cross-sectional view taken along line A-A in FIG. 2A.

FIG. 4B is a vertical cross-sectional taken along line B-B in FIG. 2B.

DETAILED DESCRIPTION

Figure 1:
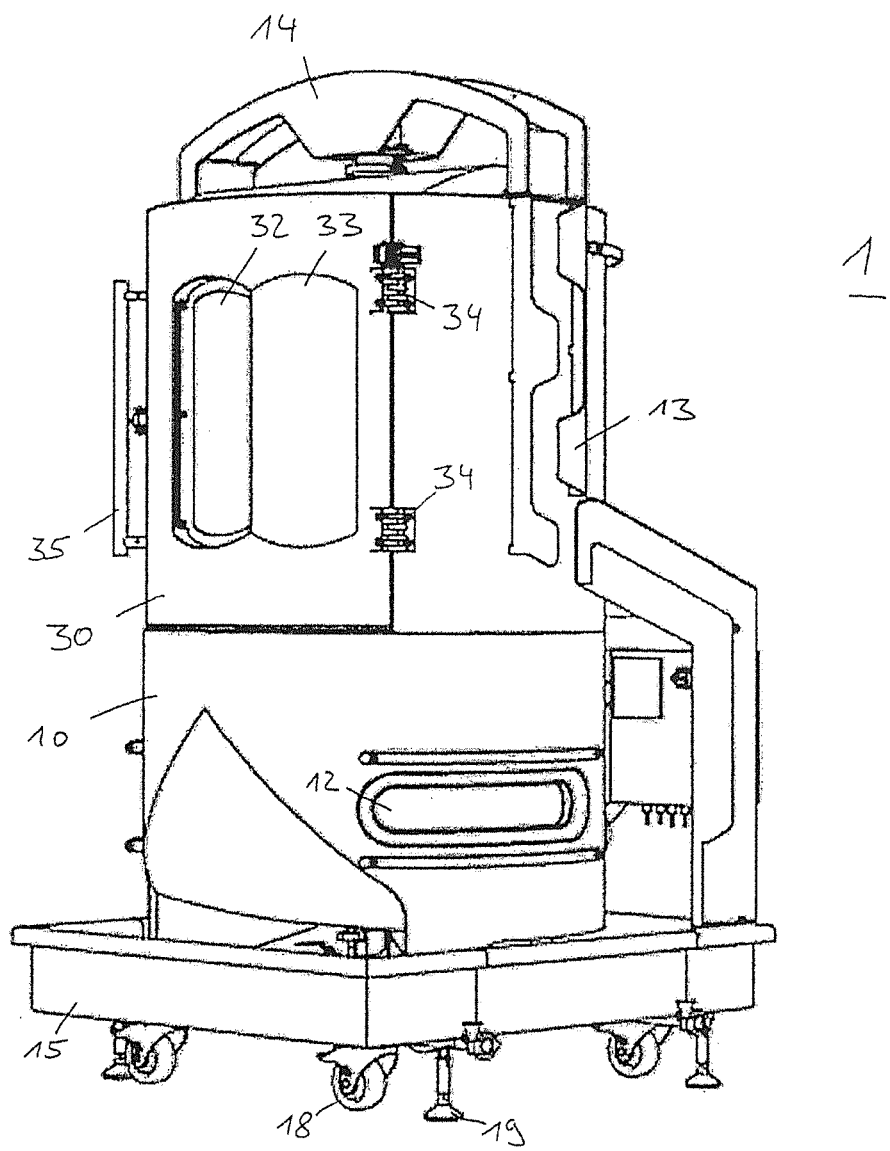
FIG. 1 is a perspective view of an apparatus for receiving a disposable bag.

FIG. 1 is a perspective view of an apparatus 1 for receiving a disposable bag. The apparatus 1 shown in the figures can be designed as a component of a system for receiving a disposable bag.

The apparatus 1 comprises a receptacle 10 which substantially has the shape of a cylinder arranged vertically—that is, with a cylinder axis arranged substantially vertically. The receptacle 10 has a receptacle interior, wherein a disposable bag which can include a biological medium, for example, can be inserted into the same. The biological medium in the disposable bag is stored in the receptacle interior of the receptacle 10 over a predetermined period of time. During the time the disposable bag with the biological medium is in the receptacle interior 10, different reactions may occur with or in the biological medium. As such, the apparatus 1 can be designed as a bioreactor.

One or several view windows are constructed in the side walls to allow monitoring of the biological medium. This and/or these allow viewing through the receptacle wall and into the receptacle interior of the receptacle 10 for observation of the biological medium. The apparatus 1 has two floor view windows 12 for this purpose, in the lower third thereof, as well as a door view window 32. The floor view windows 12 are substantially constructed in the shape of an elongated oval, the long oval axis of which is oriented substantially horizontal along the curved outer cylindrical wall of the receptacle 10. The door view window 32 is substantially constructed in the shape of an elongated rectangle, the longer sides of which are aligned substantially vertically and are constructed in the middle of a single-panel door 30 in the receptacle wall of the receptacle 10.

Figure 2A:
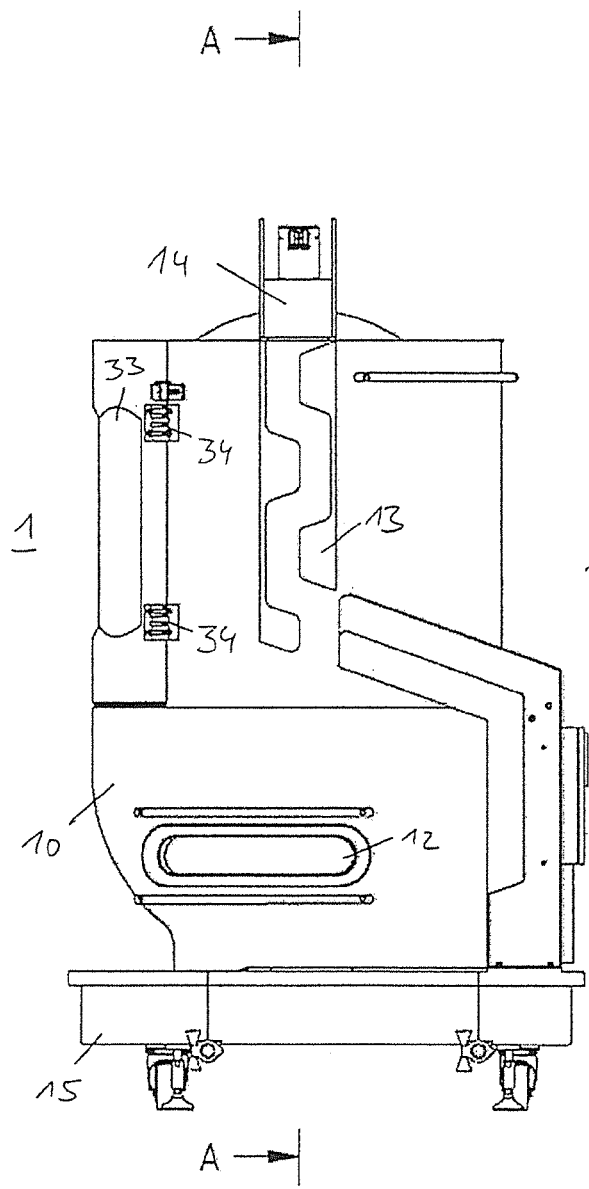
FIG. 2A is a side elevational view of an apparatus for receiving a disposable bag.
Figure 2B:
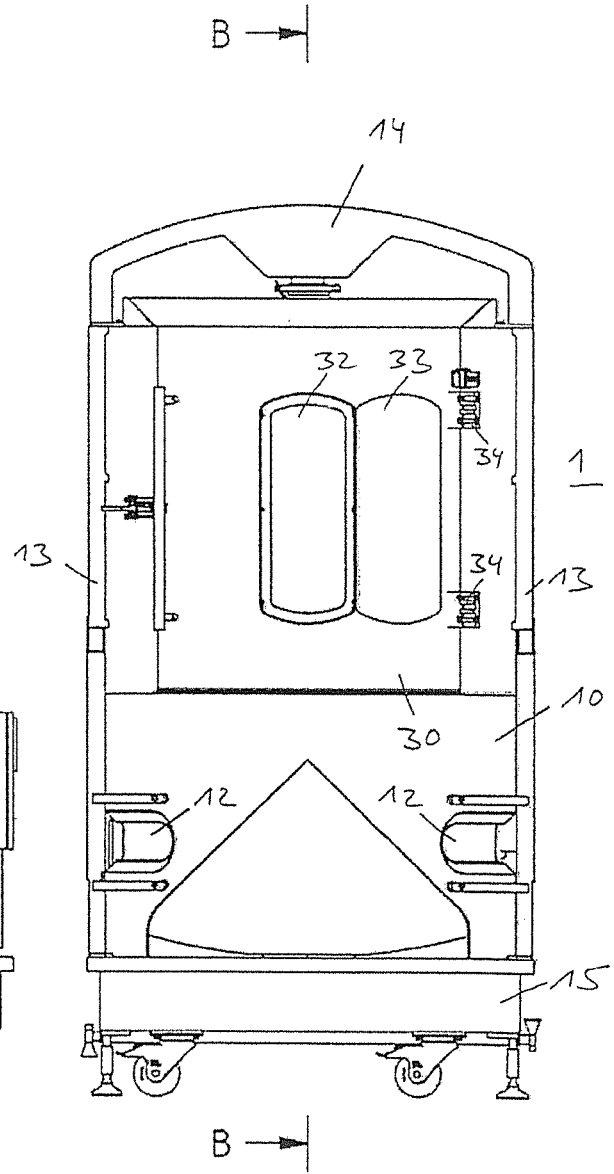
FIG. 2B is a front elevational view of an apparatus for receiving a disposable bag.

FIGS. 2A and 2B, together with FIG. 1, show various views of the apparatus 1. For example, FIG. 2B shows a frontal side view of the single-panel door 30. The single-panel door 30 is wider than long, with its longest dimension in the horizontal direction, and this width extends approximately over a cylinder segment of the receptacle 10 of about 100°. The single-panel door 30 extends in the horizontal direction along the cylinder jacket from two door hinges 34 to a door handle 35 at the opposite end of the door. The single-panel door 30 is constructed substantially in the upper two thirds of the receptacle 10, while the lower third of the receptacle 10 is substantially constructed in the form of a rigid floor bowl, which itself is not able to open. The single-panel door 30 can rotate about the door hinges 34, and therefore can be opened. If the single-panel door 30 is open, a door opening is present at a lateral position in the receptacle 10, enabling access through the same to the receptacle interior of the receptacle 10. By way of example, the disposable bag can be inserted through the door opening into the receptacle interior of the receptacle 10 from a lateral direction, in a substantially horizontal movement direction.

The apparatus 1 is mounted on casters 18 in a manner allowing rolling, wherein the apparatus can be pushed through a space on the same. In addition to the rollers 18, the apparatus 1 can have fixing feet 19 on the lower end, which enable fixing and proper alignment of the apparatus 1 on uneven floors.

The receptacle 10 is open to the top. Instead of a cylinder cover, the receptacle 10 has a stirring opening. A stirring device 14 is constructed above the receptacle 10 which is open to the top. Via the same, a stirring rod can be connected to the disposable bag, through the stirring opening, in such a manner that the interior of the disposable bag can be mixed. The stirring rod can be arranged in the interior of the disposable bag and connected to the stirring device 14 via a coupling. The stirring device 14 is placed centrally above the receptacle 10, and supported by a support bridge which lies on an upper edge of the receptacle 10 on opposite side walls of the receptacle 10.

FIG. 2A shows a side view directly onto one of the two cable ducts 13. The second of the two cable ducts 13 is arranged on the opposite outer wall of the receptacle 10. The side view of Fig, 2A shows the apparatus 1 in a position which is rotated with respect to the side view of FIG. 2B by 90°.

Figure 3:
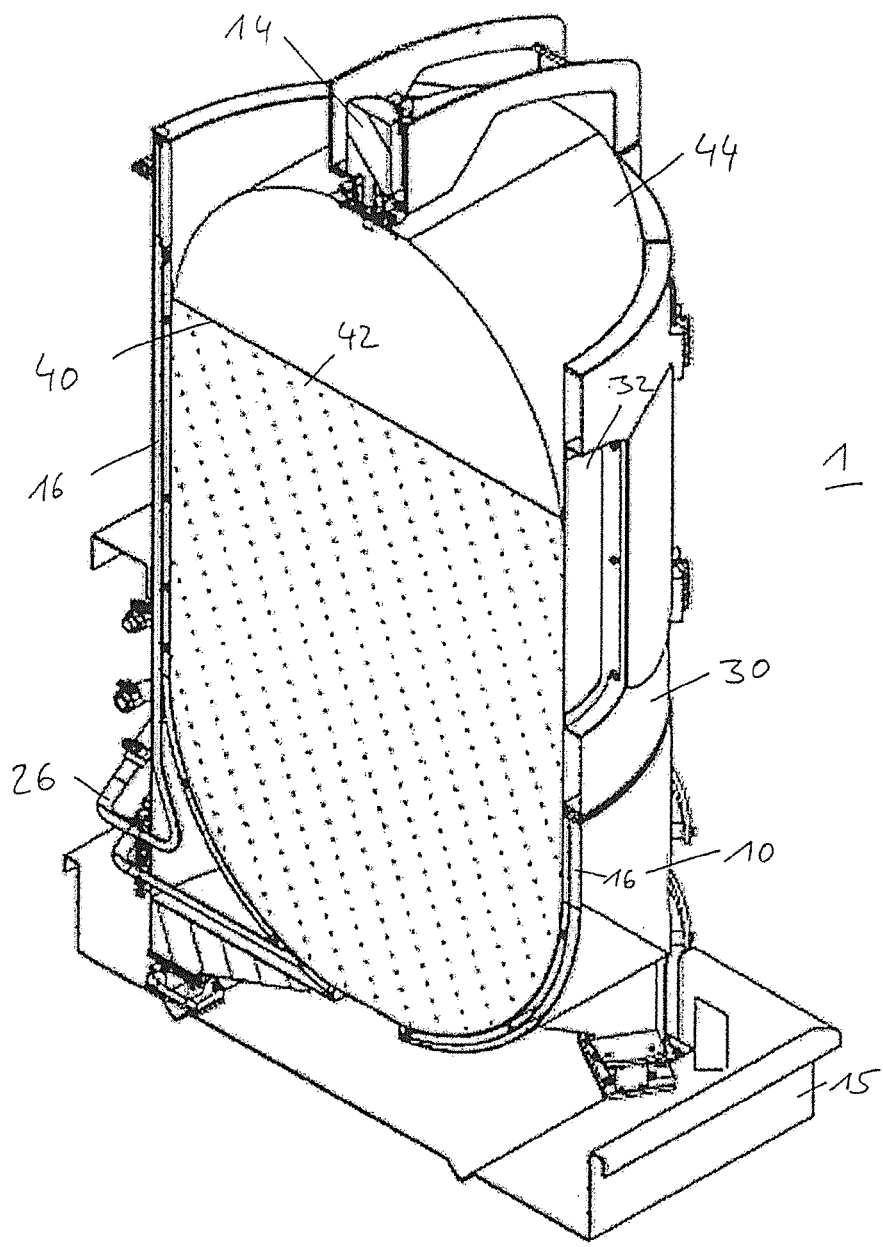
FIG. 3 is a vertical sectional view in perspective of an apparatus for receiving a disposable bag.

FIG. 3 shows a perspective illustration of a view of a vertical section through the apparatus 1. FIG. 3 shows, by way of example, a disposable bag 44—and more specifically, a cross-section of this disposable bag 44—in the receptacle interior of the receptacle 10. A biological medium 42, which is filled up to the level of a predetermined fill level 40 is arranged in the receptacle interior of the receptacle 10, and at the same time also inside the disposable bag 44. The biological medium 42 extends from the floor of the receptacle 10 up to the fill level 40, and thus fills the entire internal volume of the receptacle 10 up to the fill level 40, less the volume of the walls of the disposable bag 44, which, however, are very thin and can be considered negligible.

The shape of the disposable bag 44 is maintained by a receptacle wall 16 of the receptacle 10, which extends from the rounded floor of the receptacle 10 to above the fill level 40. The receptacle wall 16 can extend perpendicularly upwards substantially in a vertical direction at least along the upper half, but preferably along the upper two-thirds of the receptacle 10.

FIGS. 4A and 4B respectively show a vertical cross-section through the apparatus 1. A section plane A-A shown in FIG. 4A is indicated in FIG. 2A, and extends in the vertical direction through the upper part of the cable duct 13, as well as through the cylindrical center of the receptacle 10. The cross-section shown in FIG. 4B is taken in a section plane B-B which is indicated in FIG. 2B. The section plane B-B is arranged perpendicular to the section plane A-A, in a vertical direction through the cylinder axis of the receptacle 10, as well as through the center of the single-panel door 30.

The interior of the receptacle walls 16 is shown in more detail in FIGS. 4A and 4B. A hollow temperature control wall 20 is arranged on the inner walls of the receptacle 10, and a temperature control medium (not shown in the figures)

is arranged therein. The temperature control medium is regulated to be at a low pressure of less than 0.5 bar. The hollow temperature control wall 20 extends over the entire floor of the receptacle 10 and along the receptacle walls from the receptacle floor upward to above the fill level 40, up to a temperature control level 41. The temperature control level 41 is situated at substantially 1 cm to 20 cm vertically above the fill level 40.

The biological medium 42 is in direct thermal contact with the hollow temperature control wall 20, from which it is separated only by the thin wall of the disposable bag 44. The temperature of the biological medium can be controlled to a pre-definable temperature via the temperature control medium.

The apparatus 1 can particularly be designed and included for the purpose of controlling the temperature of the receptacle interior to a predetermined target temperature of about 0° C. to about 80° C., preferably about 20° C. to about 40° C.

The hollow temperature control wall 20 surrounds the receptacle interior of the receptacle 10 essentially completely, to above the fill level 40. "Essentially completely surrounds" means, in the embodiment shown in the figures, that the hollow temperature control wall 20 completely surrounds the receptacle interior up to the temperature control level 41, except for those positions where the floor view windows 12 are arranged and where the single-panel door 30 is arranged. A glass pane can be arranged at the positions of the floor view window which enable a view of the receptacle interior, and in particular the biological medium positioned in the receptacle 10 (and optionally a corresponding darkening, without temperature control). A recess in the form of the door opening in the hollow temperature control wall 20 is positioned at the location of the single-panel door 30. In an alternative embodiment, a hollow temperature control wall can also be constructed on the inside of the single-panel door 30, supplied with the temperature control medium via temperature control lines arranged on the door hinges 34.

In general, "essentially completely surrounds" means that the hollow temperature control wall 20 completely surrounds the receptacle interior up to the temperature control level 41, excluding a few predetermined positions. These few positions may be the positions where windows are arranged in the receptacle wall of the receptacle 10, and optionally where the single-panel door 30 is arranged. In general, the hollow temperature control wall 20 does not bound the receptacle interior on its upper end.

The hollow temperature control wall 20 is surrounded, on its outer side, by a hollow insulation wall 25 which contains insulation. The hollow insulation wall 25 surrounds the receptacle interior of the receptacle 10 essentially completely from the floor of the receptacle 10 up to the upper end of the receptacle wall 16 (see FIG. 3 as well). The hollow insulation wall 25 insulates both the receptacle interior, and in particular the hollow temperature control wall 20, from the outside. The insulation arranged in the hollow insulation wall 25 provides a temperature control by means of the temperature control medium which is directed inwards towards the receptacle interior, increasing the energy efficiency of the apparatus 1.

FIG. 4B shows temperature control lines 26 which are connected to the interior of the hollow temperature control wall 20. Connections and/or insulating lines used for establishing a vacuum in the hollow insulation wall are not shown in the figures.

Figure 5A:
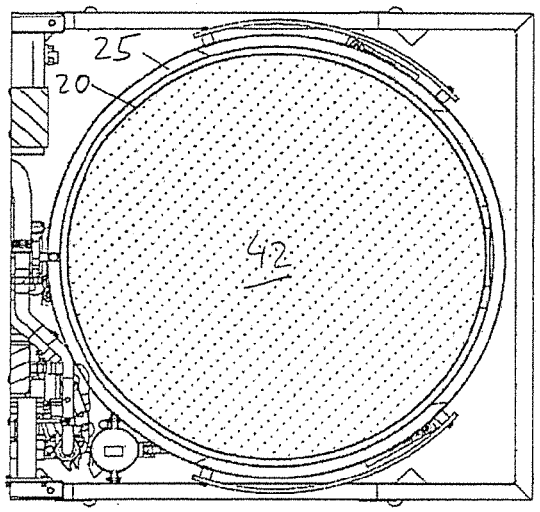
FIG. 5A is a cross-sectional view taken along line C-C in FIG. 4B.
Figure 5B:
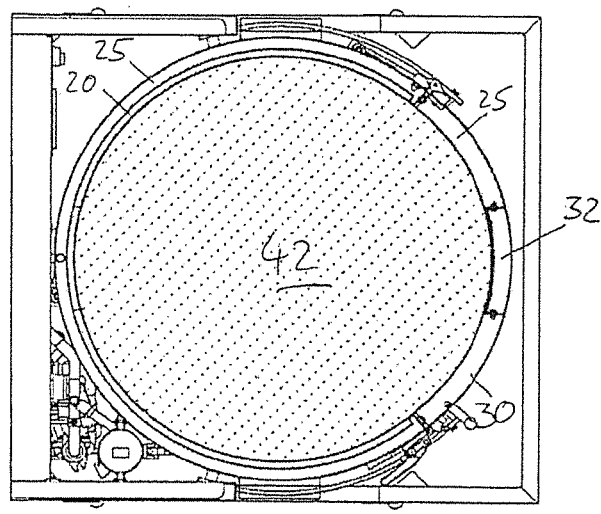
FIG. 5B is a cross-sectional view taken along line D-D in FIG. 4B.

FIGS. 5A and 5B each show a cross-section of the apparatus 1 in a horizontal sectional direction, namely through sectional planes D-D and C-C at different heights, indicated in FIG. 4B.

FIG. 5A shows a horizontal cross section through the lower third of the receptacle 10, in which the hollow temperature control wall 20 completely surrounds, and controls the temperature of, the receptacle interior, and thus the biological medium 42 arranged therein (except for the floor view window). FIG. 5A thus shows a horizontal cross-section of the lower floor trough of the receptacle 10, which cannot be opened. The hollow temperature control wall 20 is completely surrounded in the cross-section shown in FIG. 5A by the hollow insulation wall 25, and thus is insulated by the insulation arranged therein.

The horizontal cross section C-C shown in FIG. 5B is arranged above the cross-section D-D shown in FIG. 5A. The single-panel door 30 is arranged at the height of the cross-section C-C. At the position of the single-panel door 30—that is, at the position of the door opening in the receptacle wall 16—the hollow temperature control wall 20 is interrupted. At the single-panel door 30 itself, there is consequently no temperature control for the biological medium 42. At the location of the single-panel door 30, however, there is insulation in the hollow insulation wall 25, which insulates the biological medium 42—i.e., the receptacle interior of the receptacle 10—from the outside. The hollow insulation wall 25 is only interrupted at the position of the door view window 32, where the receptacle interior is only bounded by a glass pane.

The insulation thus essentially completely insulates the receptacle 10, in particular from the receptacle floor to above the fill level, up to the view windows arranged in the receptacle—which, in the embodiment, are the floor view window 12 and the door view window 32. The insulation can particularly be constructed up to the temperature control level 41, and preferably up to the upper edge of the receptacle walls 16.

The temperature control level 41 rises above both the predetermined filling level 40 and the contact surface of the disposable bag 44 with the receptacle walls 16 of the receptacle 10.

The disposable bag 44 is emptied after use—for example, via an outlet arranged below the apparatus 1—and can subsequently be completely discarded. The use of the disposable bag 44 makes it possible to omit a cleaning of the apparatus 1, and/or carry out the same much faster.

The collecting receptacle 15 functions as a collecting element for the event that, by way of example, biological medium should escape from the apparatus 1 out of a leak in the disposable bag.

Air, a vacuum, an insulating wool, a glass wool, a mineral wool, or a similar insulating material can be used as insulation in the hollow insulation wall.

The apparatus 1 has the least possible number of thermal bridges—that is, continuous metal connections from the receptacle interior to the exterior which would slow down the temperature control of the receptacle interior. The apparatus 1 only comprises heat bridges which are absolutely necessarily structurally. The temperature control medium is situated in the interior of a closed temperature control system which comprises the interior of the hollow temperature control wall 20. The temperature of the temperature control medium can be regulated and/or controlled via an internal, electrically-powered heating device, and optionally or alternatively via an external heat exchanger. The temperature control medium can be cooled and/or heated via the external heat exchanger, regardless of the internal electrical heating device of the temperature control system.

Figure 6:
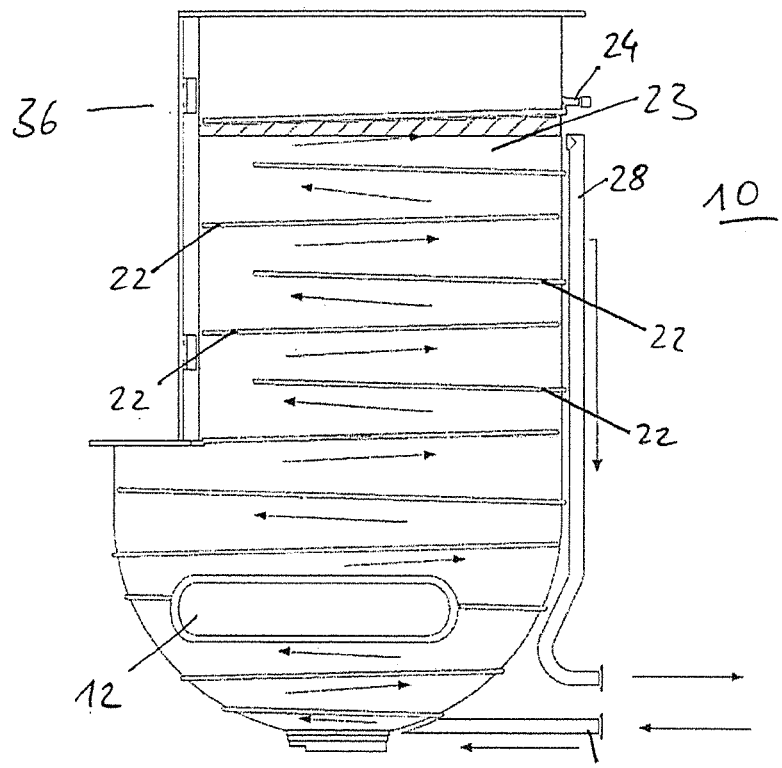
FIG. 6 is a side view of a first receptacle for receiving a disposable bag, with no door and with no outer wall.

FIG. 6 shows a side view of a first embodiment of the receptacle 10, for receiving a disposable bag, without a single-panel door 30, and without an outer wall. In other words, FIG. 6 shows a view into the interior of the hollow temperature control wall 20. As such, only one inner wall of the receptacle 10 is shown, without its outer wall, said inner wall bounding and closing off the hollow temperature control wall 20 to the outside. Also not shown is the hollow insulation wall 25, which can surround the hollow temperature control wall 20 on the outside thereof.

Inside the hollow temperature control wall 20, the receptacle 10 has multiple flow guide elements 22, which in the side view shown are arranged running in a substantially horizontal direction through the hollow temperature control wall 20. The flow guide elements 22 are designed in such a manner that they closely adjoin both the inner wall and the outer wall of the hollow temperature control wall 20. The flow guide elements 22 can be welded to, for example, both the inner wall and the outer wall of the hollow temperature control wall 20.

In this way, the flow guide elements 22 inside the hollow temperature control wall 20 define a flow channel and/or a flow guide for the temperature control medium, as indicated in FIG. 6 by arrows.

On a lower end, the hollow temperature control wall 20 has a temperature control medium inlet 27, which can be designed in the form of a connecting tube. The temperature control medium can be guided and/or brought into the hollow temperature control wall 20 via the temperature control medium inlet 27, The temperature control medium is guided from the lower end of the hollow temperature control wall 20 along the flow guide elements 22, which bound a plurality of flow sections of the flow channel running substantially horizontally.

Figures 7, 8:
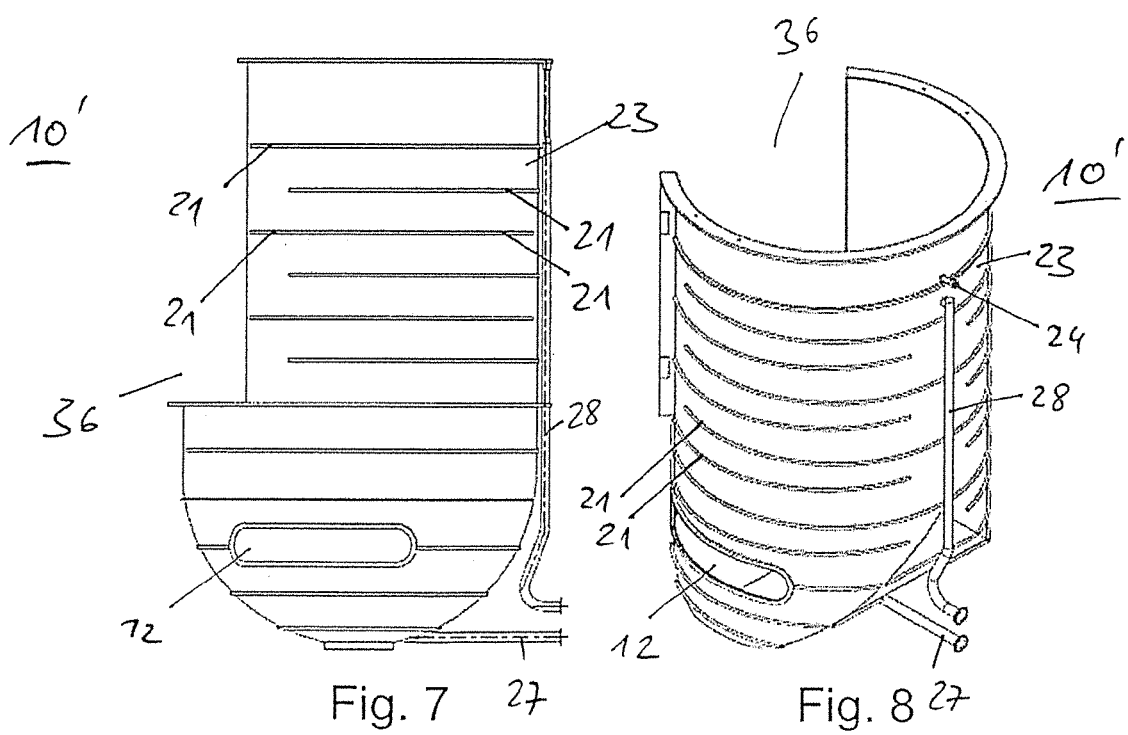
FIG. 7 is a side view of a second receptacle for receiving a disposable bag, with no door and with no outer wall.
FIG. 8 is a perspective view of a receptacle for receiving a disposable bag, with no door and with no outer wall.

In this case, the hollow temperature control wall 20 can, for example, comprise a coil-shaped flow guide element running to the receptacle interior 10. Alternatively, as shown in FIGS. 6, 7 and 8, the hollow temperature control wall 20 can have a plurality of flow guide elements 22 and/or 21 which furnish a plurality of individual, superimposed flow channel flow sections running substantially horizontally. In transition regions between these individual flow channel flow sections running substantially horizontally, the temperature control medium flows in a substantially vertical direction (substantially vertically upward in the example shown) up to the next higher flow channel flow section running substantially horizontally.

As such, the temperature control medium flows along the flow guide elements 22 into a collecting chamber 23 arranged on the upper end of the receptacle 10. The collecting chamber 23 has a temperature control medium outlet 28, from which the temperature control medium can be discharged from the hollow temperature control wall 20. The temperature control medium outlet 28 can be designed with a substantially tubular shape. An upper end of the temperature control medium outlet 28 can be designed as an overflow for the temperature control medium, and can define a maximum rise level of the temperature control medium inside the collecting chamber 23.

Above the top of the temperature control medium, air can collect in the collecting chamber 23. The air can be discharged via a ventilation outlet 24, which can also be arranged on the collecting chamber 23, separately from the temperature control medium outlet 28.

This configuration prevents or at least reduces the suction of air via the temperature control medium outlet 28 and its return into the temperature control loop, which can lead to malfunctions and disturbances of the temperature control.

The individual flow guide elements 22 are arranged, in the side view, as substantially straight separating elements. In this case, the flow guide elements 22 are oriented substantially horizontally, but face, in the side view, at an angle greater than 0° and up to 30°, preferably 1° to 10°, particularly preferably from 3° to 8°, upwards from a lower end to an upper end of the respective flow guide element 22. In other words, the flow guide elements 22 (in the side view, and when viewed from the lower end to the upper end) have a slope rising upward out of the horizontal. This beveled or inclined design of the flow guide elements 22 results in the flow channel and/or the flow guide having a vertically continuous upward direction component from the temperature control medium inlet 27 to the temperature control medium outlet 28. The flow channel thus particularly runs neither downward nor in an exclusively horizontal direction—not even partially. As a result, no air is introduced into the interior of the hollow temperature control wall 20 outside of the collecting chamber 23. At the same time, the flow guide elements 22 are still arranged in a sufficiently flat orientation—that is, substantially horizontally—that the configuration achieves an adequate horizontal distribution of the temperature control medium along the inner walls of the hollow temperature control wall 20.

FIG. 7 shows a side view of a second embodiment of the receptacle 10', for receiving a disposable bag, without a single-panel door 30, and without an outer wall. This receptacle 10' has, in the side view, flow guide elements 21 running substantially horizontally. These flow guide elements 21 are similar—aside from their substantially horizontal arrangement—to the flow guide elements 22 described above.

FIG. 7 therefore shows an alternative embodiment of the receptacle with substantially horizontal, non-tapered flow guide elements 21 (without inclination).

FIG. 8 shows, in a perspective, schematic representation, the second receptacle 10', without a single-panel door 30 and without an outer wall. Since both the floor view window 12 and the door opening 36 for the single-panel door 30 interrupt a spiral-shaped configuration of the flow guide elements 21 from bottom to top, the flow channel is substantially divided into two parts. The flow channel comprises the individual flow sections arranged substantially in a horizontal direction, on both sides of the door opening 36. A first number of flow guide elements 21 defines a first—for example, right—flow channel from the temperature control medium inlet 27 to the collecting chamber 23, and a second number of flow guide elements 21 defines a second—for example, left—flow channel from the temperature control medium inlet 27 to the collecting chamber 23, where the temperature control medium then flows out of the hollow temperature control wall 20.

In general, the flow guide elements 21 and/or 22 can define and/or bound one or more flow channels in the interior of the hollow temperature control wall 20. These flow channels can lead from a single temperature control medium inlet 27 to the same, single collecting chamber 23.

LIST OF REFERENCE NUMBERS 1 apparatus
10 receptacle
10' receptacle 12 floor view window
13 cable duct
14 stirring device
15 catch tub
16 receptacle wall
18 casters
19 fixing feet
20 hollow temperature control wall
21 flow guide element
22 flow guide element
23 collecting chamber
24 ventilation outlet
25 hollow insulation wall
26 temperature control line
27 temperature control medium inlet
28 temperature control medium outlet
30 single-panel door
32 door view window
33 door darkening
34 door hinge
35 door handle
36 door opening
40 fill level
41 temperature control level
42 biological medium
44 disposable bag

The invention claimed is:

1. An apparatus (1) for controlling a temperature of a biological medium, comprising:
  a receptacle (10) with a receptacle wall (16) defining a receptacle interior,
  a disposable bioreactor bag (44) disposed in the receptacle interior and being configured to receive the biological medium therein, a shape of the disposable bioreactor bag (44) being defined by the receptacle wall (16) of the receptacle (10),
  a hollow temperature control wall (20) that at least partially surrounds the receptacle interior of the receptacle (10), the hollow temperature control wall (20) having an interior that contains a temperature control medium, and
  an adjusting means configured to adjust a pressure of the temperature control medium in the interior of the hollow temperature control wall (20) to a maximum pressure of about 1 bar,
  wherein the hollow temperature control wall (20) holds the temperature control medium at the maximum pressure of about 1 bar, and wherein the temperature control medium controls the temperature in the disposable bioreactor bag (44) that is disposed in the receptacle interior.

2. The apparatus according to claim 1, wherein the adjusting means holds the temperature control medium in the interior of the hollow temperature control wall (20) at a pressure of about 0.20 bar to about 0.45 bar.

3. The apparatus according to claim 1, further comprising at least one flow guide element (21; 22) arranged in the hollow temperature control wall (20) for guiding the flow of the temperature control medium through the hollow temperature control wall (20).

4. The apparatus according to claim 3, wherein the at least one flow guide element (22) is inclined so that the temperature control medium flows through the hollow temperature control wall (20) with a continuous, vertical direction component.

5. The apparatus according to claim 1, further comprising a collecting chamber (23) with a ventilation outlet (24) and a temperature control medium outlet (28) that is separate from the ventilation outlet (24), the ventilation outlet (24) and the temperature control medium outlet (28) are arranged on an upper end of the hollow temperature control wall (20).

6. The apparatus according to claim 1, wherein the hollow temperature control wall (20) completely surrounds at least a lower third of the receptacle interior.

7. The apparatus according to claim 1, wherein the hollow temperature control wall (20) controls the temperature of, and/or surrounds, the receptacle interior to above a predetermined fill level (40) in the receptacle (10).

8. The apparatus according to claim 1, further comprising a relief valve for adjusting and/or limiting the pressure of the temperature control medium in the hollow temperature control wall (20).

9. The apparatus according to claim 1, further comprising an electric heater that exchanges heat with the temperature control medium.

10. The apparatus according to claim 1, further comprising tubing that conveys the temperature control medium through an external heat exchanger.

11. The apparatus according to claim 1, further comprising an insulation at least partially formed on a side of the hollow temperature control wall (20) facing away from the receptacle interior, the insulation insulating the hollow temperature control wall (20) from the outside.

12. The apparatus according to claim 11, wherein the insulation is at least partially arranged in a hollow insulation wall (25) formed on the side of the hollow temperature control wall (20) facing away from the receptacle interior.

13. The apparatus according to claim 1, wherein the receptacle (10) has an openable door (30) through which the disposable bag (44) can be inserted into the receptacle interior in a substantially horizontal plane.

14. The apparatus according to claim 13, wherein the receptacle (10) is a substantially vertical cylinder, and the door (30) of the receptacle (10) is constructed over a cylindrical sector of about 80° to about 150°.

* * * * *